United States Patent
Truschel

(10) Patent No.: US 9,950,132 B2
(45) Date of Patent: Apr. 24, 2018

(54) SYSTEMS AND METHODS TO DETERMINE THE FRACTION OF INHALED OXYGEN DURING VENTILATION

(71) Applicant: KONINKLIJKE PHILIPS N.V., Eindhoven (NL)

(72) Inventor: William Anthony Truschel, Oakmont, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 681 days.

(21) Appl. No.: 14/398,925

(22) PCT Filed: Apr. 23, 2013

(86) PCT No.: PCT/IB2013/053196
§ 371 (c)(1),
(2) Date: Nov. 4, 2014

(87) PCT Pub. No.: WO2013/168036
PCT Pub. Date: Nov. 14, 2013

(65) Prior Publication Data
US 2015/0107593 A1    Apr. 23, 2015

Related U.S. Application Data

(60) Provisional application No. 61/645,825, filed on May 11, 2012.

(51) Int. Cl.
A61M 16/00    (2006.01)
A61M 16/16    (2006.01)
(Continued)

(52) U.S. Cl.
CPC ....... A61M 16/1005 (2014.02); A61B 5/0833 (2013.01); A61B 5/091 (2013.01);
(Continued)

(58) Field of Classification Search
CPC .......... A61M 16/1005; A61M 16/0003; A61M 16/0069; A61M 16/04; A61M 16/0666; A61B 5/0833; A61B 5/091; A61B 5/097
See application file for complete search history.

(56) References Cited

U.S. PATENT DOCUMENTS

| 4,340,044 A | 7/1982 | Levy |
| 6,123,074 A * | 9/2000 | Hete ................ A61M 16/12 128/203.14 |

(Continued)

FOREIGN PATENT DOCUMENTS

| CN | 101365509 A | 2/2009 |
| CN | 101365510 A | 2/2009 |

(Continued)

OTHER PUBLICATIONS

Yoder E.A. et al., "Inspired Oxygen Concentrations During Positive Pressure Therapy", Sleep and Breathing ; International Journal of the Science and Practice of Sleep Medicine, Springer, Berlin, DE, vol. 8, No. 1, Jan. 1, 2004 (Jan. 1, 2004), pp. 1-5, XP019360535.
(Continued)

*Primary Examiner* — Tan-Uyen (Jackie) T Ho
*Assistant Examiner* — Jonathan Paciorek
(74) *Attorney, Agent, or Firm* — Michael W. Haas

(57) ABSTRACT

Systems and methods to estimate, on a breath-by-breath basis, the fraction of inhaled oxygen during ventilation of a subject. The fraction of inhaled oxygen may be based on exhaled tidal volume, a volume of dead space within the subject interface, leaked exhalation volume, and subsequently inhaled tidal volume and leaked inhalation volume.

15 Claims, 2 Drawing Sheets

(51) Int. Cl.
*A61M 16/10* (2006.01)
*A61B 5/083* (2006.01)
*A61B 5/097* (2006.01)
*A61B 5/091* (2006.01)
*A61M 16/06* (2006.01)
*A61M 16/04* (2006.01)

(52) U.S. Cl.
CPC ......... *A61B 5/097* (2013.01); *A61M 16/0003* (2014.02); *A61M 16/0051* (2013.01); *A61M 16/0069* (2014.02); *A61M 16/04* (2013.01); *A61M 16/0666* (2013.01); *A61M 16/0066* (2013.01); *A61M 16/161* (2014.02); *A61M 2016/003* (2013.01); *A61M 2016/0021* (2013.01); *A61M 2016/0027* (2013.01); *A61M 2016/0033* (2013.01); *A61M 2016/102* (2013.01); *A61M 2016/103* (2013.01); *A61M 2016/1025* (2013.01); *A61M 2205/15* (2013.01); *A61M 2205/18* (2013.01); *A61M 2205/3334* (2013.01); *A61M 2205/3365* (2013.01); *A61M 2205/3368* (2013.01); *A61M 2205/502* (2013.01)

(56) References Cited

U.S. PATENT DOCUMENTS

| | | | |
|---|---|---|---|
| 6,512,938 B2 * | 1/2003 | Claure | A61M 16/0051 600/322 |
| 6,752,150 B1 | 6/2004 | Remmers | |
| 7,788,963 B2 | 9/2010 | Orr | |
| 8,402,967 B2 | 3/2013 | Smith | |
| 8,485,183 B2 | 7/2013 | Masic | |
| 9,516,875 B2 | 12/2016 | Fishman | |
| 2003/0084901 A1 | 5/2003 | Martinez | |
| 2004/0211423 A1* | 10/2004 | Baecke | A61M 16/024 128/204.23 |
| 2004/0216740 A1 | 11/2004 | Remmers | |
| 2007/0129647 A1 | 6/2007 | Lynn | |
| 2008/0202518 A1 | 8/2008 | Mitton | |
| 2009/0107500 A1* | 4/2009 | Edwards | A61M 16/10 128/204.23 |
| 2009/0241951 A1 | 10/2009 | Jafari | |
| 2009/0253995 A1 | 10/2009 | Lewis | |
| 2010/0051030 A1 | 3/2010 | Richard | |
| 2010/0300445 A1 | 12/2010 | Cahetburn | |
| 2012/0006326 A1 | 1/2012 | Ahmad | |
| 2012/0090611 A1 | 4/2012 | Graboi | |
| 2013/0267863 A1 | 10/2013 | Orr | |

FOREIGN PATENT DOCUMENTS

| | | |
|---|---|---|
| CN | 101529232 A | 9/2009 |
| CN | 101977649 A | 2/2011 |
| CN | 102056538 A | 5/2011 |
| CN | 103379856 A | 10/2013 |
| JP | 2007518497 A | 7/2007 |
| JP | 2010531685 A | 9/2010 |
| JP | 2011516159 A | 5/2011 |
| WO | WO2007026367 A2 | 3/2007 |
| WO | WO2009003488 A2 | 1/2009 |
| WO | WO2009058081 A1 | 5/2009 |
| WO | WO2009123981 A1 | 10/2009 |
| WO | WO2010140072 A1 | 12/2010 |
| WO | WO2010150264 A1 | 12/2010 |
| WO | WO2012014106 A1 | 2/2012 |

OTHER PUBLICATIONS

Tsai-Hsin Chen et al., "The Relation Between Oxygen Consumption and the Equilibrated Inspired Oxygen Fraction in an Anesthetic Circle Breathing System: A Mathematic Formulation & Laboratory Simulations", Annals of Biomedical Engineering, vol. 37, No. 1, Jan. 1, 2009 (Jan. 1, 2009), pp. 246-254, XP055024676.

* cited by examiner

US 9,950,132 B2

SYSTEMS AND METHODS TO DETERMINE THE FRACTION OF INHALED OXYGEN DURING VENTILATION

CROSS-REFERENCE TO RELATED APPLICATIONS

This patent application claims the priority benefit under 35 U.S.C. § 371 of international patent application no. PCT/IB2013/053196, filed Apr. 23, 2013, which claims the priority benefit under 35 U.S.C. § 119(e) of U.S. Provisional Application No. 61/645,825 filed on May 11, 2012, the contents of which are herein incorporated by reference.

BACKGROUND OF THE INVENTION

1. Field of the Invention

The present disclosure pertains to systems and methods to determine and/or estimate the fraction of inhaled oxygen on a breath-by-breath basis during ventilation of a subject.

2. Description of the Related Art

Various systems for ventilating patients are known. The concept of dead space within a respiratory/ventilation system is known, in particular, within a subject interface and/or a subject interface appliance. It is known that exhaled air has an increased mole fraction of carbon dioxide and a reduced mole fraction of oxygen compared to inhaled air. Various systems for expelling exhaled carbon dioxide from a respiratory/ventilation system are known. It is known that prolonged exposure during respiration to elevated levels of carbon dioxide or reduced levels of oxygen within the flow of breathed gas is, at the least, uncomfortable for patients.

SUMMARY

Accordingly, one or more aspects of the present disclosure relate to a ventilator. The ventilator comprises a pressure generator configured to generate a pressurized flow of breathable gas for delivery to an airway of the subject; a subject interface configured to guide the pressurized flow of breathable gas to the airway of the subject, wherein the subject interface includes a volume of dead space; one or more sensors configured to generate output signals conveying information related to flow rate and/or pressure in the subject interface; and one or more processors configured to execute computer program modules. The computer program modules comprise a control module configured to control the pressure generator to generate the pressurized flow of breathable gas to at least partially mechanically ventilate the subject; a parameter determination module and an estimation module. The parameter determination module is configured to determine, based on the output signals generated during an exhalation, an exhaled tidal volume and a leaked exhalation volume, and to determine, based on the output signals generated during a subsequent inhalation, an inhaled tidal volume and a leaked inhalation volume. The estimation module is configured to estimate a fraction of inhaled oxygen during the subsequent inhalation based on a first comparison of the exhaled tidal volume with a combination of the volume of dead space and the leaked exhalation volume, and further based on a second comparison of the inhaled tidal volume with a combination of the volume of dead space and the leaked inhalation volume.

Yet another aspect of the present disclosure relates to a method of providing ventilation to a subject. The method comprises generating a pressurized flow of breathable gas for delivery to an airway of the subject; guiding the pressurized flow of breathable gas to the airway of the subject through a volume of dead space; generating one or more output signals by one or more sensors conveying information related to flow rate and/or pressure of the pressurized flow of breathable gas; controlling the pressurized flow of breathable gas to at least partially mechanically ventilate the subject; determining, based on the output signals generated during an exhalation, an exhaled tidal volume and a leaked exhalation volume; determining, based on the output signals generated during a subsequent inhalation, an inhaled tidal volume and a leaked inhalation volume; and estimating a fraction of inhaled oxygen during the subsequent inhalation based on a first comparison of the exhaled tidal volume with a combination of the volume of dead space and the leaked exhalation volume, and further based on a second comparison of the inhaled tidal volume with a combination of the volume of dead space and the leaked inhalation volume.

Still another aspect of present disclosure relates to a system configured for providing ventilation to a subject. The system comprises a means for generating a pressurized flow of breathable gas for delivery to an airway of the subject; means for guiding the pressurized flow of breathable gas through a volume of dead space to the airway of the subject; sensor means for generating one or more output signals conveying information related to flow rate and/or pressure of the pressurized flow of breathable gas; control means for controlling the pressure means to at least partially mechanically ventilate the subject; means for determining, based on the output signals generated during an exhalation, an exhaled tidal volume and a leaked exhalation volume; means for determining, based on the output signals generated during a subsequent inhalation, an inhaled tidal volume and a leaked inhalation volume; and estimating means for estimating a fraction of inhaled oxygen during the subsequent inhalation based on a first comparison of the exhaled tidal volume with a combination of the volume of dead space and the leaked exhalation volume, and further based on a second comparison of the inhaled tidal volume with a combination of the volume of dead space and the leaked inhalation volume.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
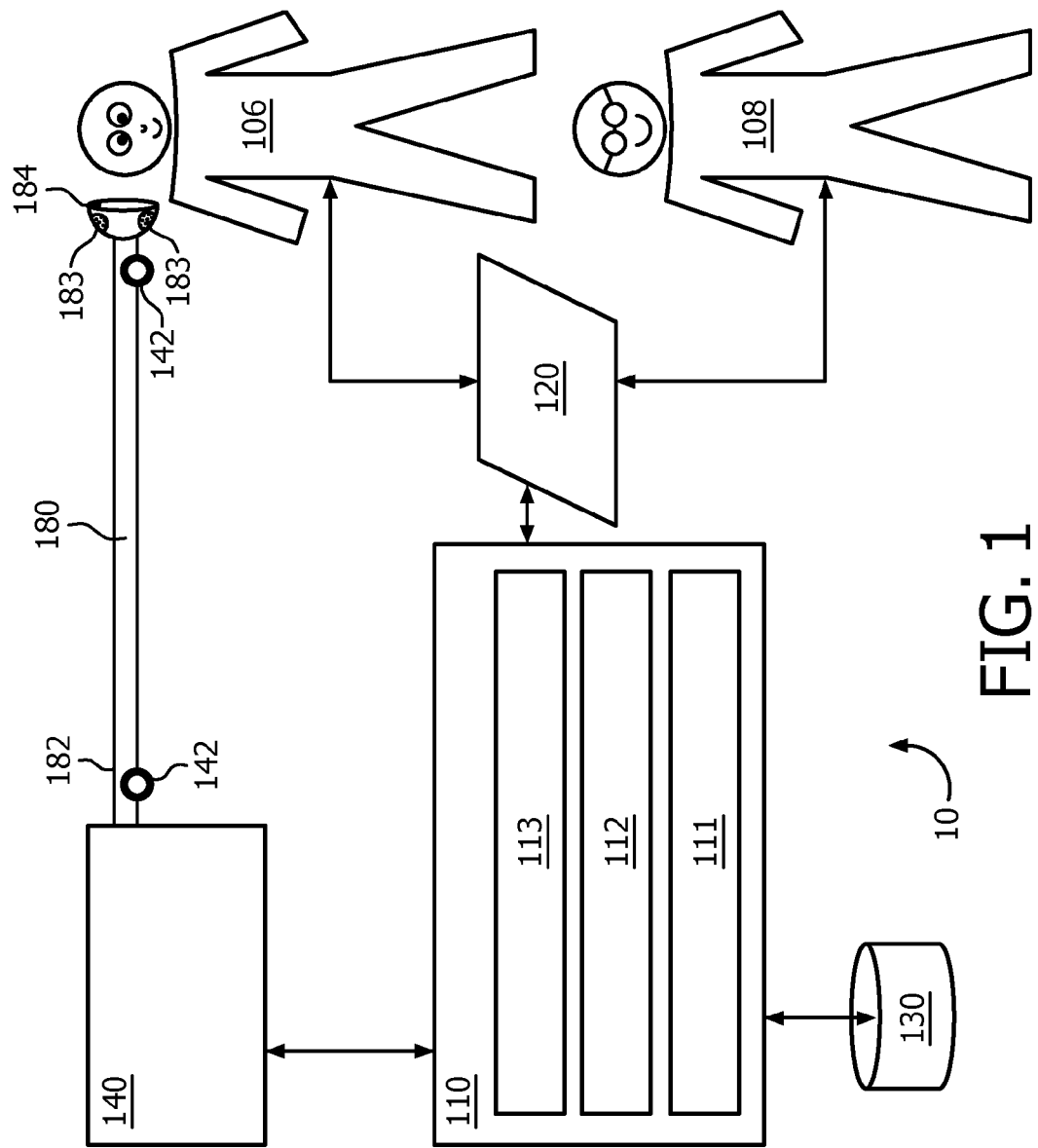
FIG. 1 schematically illustrates a system configured to ventilate a subject, according to one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates an exemplary embodiment of a system 10 to ventilate a subject 106. System 10 includes one or more of a pressure generator 140, a user interface 120, a delivery circuit 180, electronic storage 130, one or more sensors 142, one or more leak ports 183, one or more processors 110, a control module 111, a parameter determination module 112, an estimation module 113, and/or other components.

Pressure generator 140 of system 10 in FIG. 1 may be integrated, combined, or connected with a ventilator system. Pressure generator 140 may be configured to provide a pressurized flow of breathable gas for delivery to the airway of subject 106, e.g. via delivery circuit 180, to effect mechanical ventilation of subject 106, and/or to provide other therapeutic benefits. Typically, mechanical ventilation is provided to subjects not capable of properly breathing due to respiratory muscle weakness, neuromuscular disease, atrophy, and/or dysfunction. Subject 106 may or may not initiate one or more phases of respiration. For example, one or more embodiments may include active ventilation during inspiration and passive ventilation during exhalation.

During inspiration, the pressure of the pressurized flow of breathable gas may be adjusted to one or more inspiratory pressure levels to induce, support, and/or control inhalation by subject 106. Alternatively, and/or additionally, during expiration, the pressure of the pressurized flow of breathable gas may be adjusted to one or more expiratory pressure levels to induce, support, and/or control exhalation by subject 106. Pressure generator 140 is configured to adjust one or more of a pressure level, flow rate, humidity, velocity, acceleration, and/or other parameters of the pressurized flow of breathable gas.

A pressurized flow of breathable gas is delivered from pressure generator 140 to the airway of subject 106 via a delivery circuit 180. Delivery circuit 180 may be configured to selectively control the direction and/or flow of breathable gas to and/or from the airway of subject 106. Delivery circuit 180 may be referred to as subject interface 180. Delivery circuit 180 may be configured to permit gas to be exhausted from the airway of subject 106 through delivery circuit 180 and/or any of its constituent components, e.g. to ambient atmosphere.

Delivery circuit 180 may include a conduit 182, one or more leak ports 183, a subject interface appliance 184, and/or other constituent components. Delivery circuit 180 and/or any of its constituent components may include, individually and/or jointly, a volume of dead space. For example, in some embodiments, at least some of the volume within subject interface appliance 184 may be part of the afore-mentioned volume of dead space. This volume of dead space may be referred to as $V_{ds}$.

Conduit 182 includes a flexible length of hose, or other conduit, either in a single-limb or multi-limb configuration that places subject interface appliance 184 in fluid communication with pressure generator 140. Conduit 182 forms a flow path through which the pressurized flow of breathable gas (e.g. air) is communicated between subject interface appliance 184 and pressure generator 140. In some embodiments, at least some of the volume within conduit 182 may be part of the afore-mentioned volume of dead space $V_{ds}$.

One or more leak ports 183, formed in delivery circuit 180, are configured to provide fluid communication between at least part of an interior of delivery circuit 180 and ambient atmosphere to facilitate mechanical ventilation. A leak port may be referred to as an exhalation port, a leak device, or an exhalation device. The mechanical ventilation through one or more leak ports 183 may be passive. Fluid communication through a leak port may be intentional, e.g. to facilitate the removal of exhaled gas from system 10. In some embodiments, the one or more leak ports 183 are sufficiently large to allow gas to escape fast enough that a reduction in pressure of the pressurized flow of breathable gas induces exhalation. Although two leak ports 183 are depicted in FIG. 1, this exemplary depiction is not intended to be limiting in any way. In some embodiments, a leak port may include on or more of an orifice, an opening, a selectively closable opening, a partially closeable opening, a fluid connector, and/or other ways to fluidly communicate between an interior of delivery circuit 180 and ambient atmosphere to facilitate mechanical ventilation. Although leak ports 183 are depicted in FIG. 1 as integrated within subject interface appliance 184, this embodiment is exemplary and not intended to be limiting in any way. For example, leak ports may be disposed elsewhere in delivery circuit 180 and/or system 10.

Subject interface appliance 184 of system 10 in FIG. 1 is configured to deliver the pressurized flow of breathable gas to the airway of subject 106. As such, subject interface appliance 184 may include any appliance suitable for this function. In some embodiments, pressure generator 140 is a dedicated ventilation device and subject interface appliance 184 is configured to be removably coupled with another interface appliance being used to deliver respiratory therapy to subject 106. For example, subject interface appliance 184 may be configured to engage with and/or be inserted into an endotracheal tube, a tracheotomy portal, and/or other interface appliances. In one embodiment, subject interface appliance 184 is configured to engage the airway of subject 106 without an intervening appliance. In this embodiment, subject interface appliance 184 may include one or more of an endotracheal tube, a nasal cannula, a tracheotomy tube, a nasal mask, a nasal/oral mask, a full-face mask, a total facemask, and/or other interface appliances that communicate a flow of gas with an airway of a subject. The present disclosure is not limited to these examples, and contemplates delivery of the pressurized flow of breathable gas to subject 106 using any subject interface.

Electronic storage 130 of system 10 in FIG. 1 comprises electronic storage media that electronically stores information. The electronic storage media of electronic storage 130 may include one or both of system storage that is provided integrally (i.e., substantially non-removable) with system 10 and/or removable storage that is removably connectable to system 10 via, for example, a port (e.g., a USB port, a FireWire port, etc.), a slot (e.g., an SD card slot, etc.), or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 10 to function properly. For example, electronic storage 130 may record or store information pertaining to occurrences of the fraction of inhaled oxygen breaching a predetermined minimum oxygen threshold (as discussed elsewhere herein), and/or other information. Electronic storage 130 may be a separate component within system 10, or electronic storage 130 may be provided integrally with one or more other components of system 10 (e.g., processor 110).

User interface 120 of system 10 in FIG. 1 is configured to provide an interface between system 10 and a user (e.g., user 108, subject 106, a caregiver, a therapy decision-maker, etc.) through which the user can provide information to and receive information from system 10. This enables data, results, and/or instructions and any other communicable items, collectively referred to as "information," to be communicated between the user and system 10. An example of information that may be conveyed to user 108 is a warning when the fraction of inhaled oxygen breaches a predetermined minimum oxygen threshold during ventilation. Examples of interface devices suitable for inclusion in user interface 120 include a keypad, buttons, switches, a keyboard, knobs, levers, a display screen, an electronic display configured to display information, a touch screen, speakers, a microphone, an indicator light, an audible alarm, and a printer. Information may be provided to user 108 or subject 106 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 10 from removable storage (e.g., a smart card, a flash drive, a removable disk, etc.) that enables the user(s) to customize system 10. Other exemplary input devices and techniques adapted for use with system 10 as user interface 120 include, but are not limited to, an RS-232 port, RF link, an IR link, modem (telephone, cable, Ethernet, internet or other). In short, any technique for communicating information with system 10 is contemplated as user interface 120.

One or more sensors 142 of system 10 in FIG. 1 are configured to generate output signals conveying measurements related to gas parameters. These gas parameters may include one or more of flow rate, (airway) pressure, humidity, velocity, acceleration, and/or other gas or respiratory parameters. These parameters may pertain to one or more gas levels of the pressurized flow of breathable gas provided through pressure generator 140 and/or a flow of gas at or near the airway of subject 106, for example within delivery circuit 180. One or more sensors 142 may be in fluid communication with conduit 182 and/or subject interface appliance 184.

The illustration of sensor 142 including two members in FIG. 1 is not intended to be limiting. The illustration of a sensor 142 at or near subject interface appliance 184 is not intended to be limiting. The illustration of a sensor 142 at or near pressure generator 140 is not intended to be limiting. In one embodiment sensor 142 includes a plurality of sensors operating as described above by generating output signals conveying information related to parameters associated with the state and/or condition of an airway of subject 106, the breathing of subject 106, the gas breathed by subject 106, the composition of the gas breathed by subject 106, the delivery of the gas to the airway of subject 106, and/or a respiratory effort by the subject. For example, a parameter may be related to a mechanical unit of measurement of a component of pressure generator 140 (or of a device that pressure generator 140 is integrated, combined, or coupled with) such as valve drive current, rotor speed, motor speed, blower speed, fan speed, or a related measurement that may serve as a proxy for any of the previously listed parameters through a previously known and/or calibrated mathematical relationship. Resulting signals or information from one or more sensors 142 may be transmitted to processor 110, user interface 120, electronic storage 130, and/or other components of system 10. This transmission may be wired and/or wireless.

Processor 110 of system 10 in FIG. 1 is configured to provide information processing capabilities in system 10. As such, processor 110 includes one or more of a digital processor, an analog processor, a digital circuit designed to process information, an analog circuit designed to process information, a state machine, and/or other mechanisms for electronically processing information. Although processor 110 is depicted in FIG. 1 as a single entity, this is for illustrative purposes only. In some embodiments, processor 110 includes a plurality of processing units.

As is shown in FIG. 1, processor 110 is configured to execute one or more computer program modules. The one or more computer program modules include one or more of control module 111, parameter determination module 112, estimation module 113, and/or other modules. Processor 110 may be configured to execute modules 111-113 by software; hardware; firmware; some combination of software, hardware, and/or firmware; and/or other mechanisms for configuring processing capabilities on processor 110.

It should be appreciated that although modules 111-113 are illustrated in FIG. 1 as being co-located within a single processing unit, in embodiments in which processor 110 includes multiple processing units, one or more of modules 111-113 may be located remotely from the other modules. The description of the functionality provided by the different modules 111-113 described herein is for illustrative purposes, and is not intended to be limiting, as any of modules 111-113 may provide more or less functionality than is described. For example, one or more of modules 111-113 may be eliminated, and some or all of its functionality may be incorporated, shared, integrated into, and/or otherwise provided by other ones of modules 111-113. Note that processor 110 may be configured to execute one or more additional modules that may perform some or all of the functionality attributed below to one of modules 111-113.

Control module 111 of system 10 in FIG. 1 is configured to control operation of system 10 to at least partially mechanically ventilate subject 106. Mechanically ventilating subject 106 may include adjusting pressure levels to induce, support, and/or control one or both of inhalation and/or exhalation by subject 106. Control module 111 may be configured to control the pressure generator to adjust one or more levels of one or more gas parameters of the pressurized flow of breathable gas in accordance with one or more of a (respiratory) therapy regimen, one or more algorithms that control adjustments and/or changes in the pressurized flow of breathable gas, and/or other factors. Control module 111 may be configured to control pressure generator 140 such that one or more gas parameters of the pressurized flow of breathable gas are varied over time in accordance with a respiratory therapy regimen and/or treatment. Control module 111 may be configured to control pressure generator 140 to provide the pressurized flow of breathable gas at inspiratory pressure levels during inhalation phases, and/or at expiratory pressure levels during exhalation phases (e.g. positive end expiratory pressure, or PEEP). Parameters determined by parameter determination module 112 and/or received through one or more sensors 142 may be used by control module 111, e.g. in a feedback manner, to adjust therapy modes/settings/operations of system 10. Alternatively, and/or simultaneously, signals and/or information received through user interface 120 may be used by control module 111, e.g. in a feedback manner, to adjust one or more therapy modes/settings/operations of system 10.

In some embodiments, user 108 and/or subject 106 may (e.g. manually) control one or more pressure levels used during operation of system 10, e.g. through user interface 120. Control module 111 may be configured to time its operations relative to the transitional moments in the breathing cycle of a subject, over multiple breath cycles, and/or in any other relation to any detected events and/or occurrences during operation of system 10.

In some embodiments, operation of control module 111 may be governed through programmatic control, e.g. by an algorithm implemented through instructions that are executed by control module 111. Such an algorithm may be designed to titrate operating conditions of system 10 such that a target operating condition is reached and/or accomplished over time. For example, the algorithm may use a target inhalation tidal volume (e.g. inhaled tidal volume) for individual inhalations. The algorithm may adjust one or more gas parameters of the pressurized flow of breathable gas accordingly, such as, e.g., inspiratory pressure level and/or inhalation period.

Parameter determination module 112 of system 10 in FIG. 1 is configured to determine one or more gas parameters, respiratory parameters, and/or other parameters from output signals generated by sensor(s) 142. The one or more gas parameter may include and/or be related to one or more of (peak) flow, flow rate, (tidal) volume, pressure, temperature, humidity, velocity, acceleration, gas composition (e.g. concentration(s) of one or more constituents such as, e.g., $CO_2$), thermal energy dissipated, (intentional) gas leak, and/or other measurements related to the (pressurized) flow of breathable gas. One or more respiratory parameters may be derived from gas parameters and/or other output signals conveying measurements of the pressurized flow of breathable gas. The one or more respiratory parameters may include one or more of respiratory rate, breathing period, inhalation time or period, exhalation time or period, respiration flow curve shape, transition time from inhalation to exhalation and/or vice versa, transition time from peak inhalation flow rate to peak exhalation flow rate and/or vice versa, respiration pressure curve shape, maximum proximal pressure drop (per breathing cycle and/or phase), peak cough flow, average (or otherwise aggregated) cough flow, inhaled tidal volume (per inhalation), exhaled tidal volume (per exhalation), leaked exhalation volume (e.g. through one or more leak ports 183, per exhalation), leaked inhalation volume (e.g. through one or more leak ports 183, per inhalation), and/or other respiratory parameters. Parameters may be determined on a breath-by-breath basis, on a cough-by-cough basis, per individual respiratory phase, and/or at other intervals.

In some embodiments, parameter determination module 112 may be configured to determine and/or estimate a leak in delivery circuit 180 and/or another component of system 10. As used herein a leak may be intentional (e.g. through one or more leak ports 183) or unintentional (e.g. at or near the engagement of subject interface appliance 184 and the airway of subject 106). For example, leaks may refer to fluid communication between (the interior of) any component of system 10 and ambient air. During exhalations, parameter determination module 112 may be configured to determine, based on the generated output signals, a leaked exhalation volume, e.g. through one or more leak ports 183. During inhalations, parameter determination module 112 may be configured to determine, based on the generated output signals, a leaked inhalation volume, e.g. through one or more leak ports 183. Leak flow rate $Q_{leak}$ may be approximated using the following version of the Blasius equation:

$$Q_{leak} = 6.3 \cdot P^{4/7}, \text{ for delivered pressure, } P$$

The leaked exhalation volume is based on, at least, leak flow rate $Q_{leak}$ and the duration of exhalation. The leaked inhalation volume is based on, at least, leak flow rate $Q_{leak}$ and the duration of inhalation. Depending on the nature, shape, location, and/or size of leak ports 183, parameter determination module 112 may be configured to compensate accordingly when determining parameters that are related to a leak in system 10.

Estimation module 113 is configured to estimate a fraction of inhaled oxygen $FiO_2$ during inhalations. To begin, for individual exhalations, a mole fraction of oxygen within the volume of dead space $V_{ds}$ is determined and/or estimated based on a comparison of an individual exhalation tidal volume $V_{te}$ with a combination of the leaked exhalation volume $\int Q_{leak}$ during a particular individual exhalation and $V_{ds}$. In some embodiments, mole fractions of oxygen of inhaled air $\chi_{air}$ and exhaled air $\chi_{vte}$ may be assumed to be 0.21 and 0.16, respectively. Note that other operating conditions are contemplated within the scope of this disclosure, including the use of oxygen-enriched breathable gas within system 10. The mole fraction of oxygen within the volume of dead space at the end of an individual exhalation or at the start of the subsequent inhalation may be referred to as $\chi_{start\_of\_insp}$. Note that embodiments that compensate for leaking of breathable gas from $V_{ds}$ during periods between inhalations and exhalations (and/or vice versa) are contemplated within the scope of this disclosure. $\chi_{start\_of\_insp}$ may be approximated using the following equation:

$$\chi_{start\_of\_insp} = \frac{V_{te} \cdot \chi_{vte} + (V_{tot\_exp} - V_{te})\chi_{air}}{V_{tot\_exp}} \quad \ldots \quad V_{te} \leq \left(V_{ds} + \int_{expiration} Q_{leak}\right)$$

$$\chi_{start\_of\_insp} = \chi_{vte} \quad \ldots \quad V_{te} > \left(V_{ds} + \int_{expiration} Q_{leak}\right)$$

In the preceding equation, total exhalation volume $V_{tot\_exp}$ may be approximated using the following equation:

$$V_{tot\_exp} = V_{te} + V_{ds} + \int_{expiration} Q_{leak}$$

In some embodiments, ideal blending within volume of dead space $V_{ds}$ may be assumed. Note that other operating conditions are contemplated within the scope of this disclosure, including imperfect blending of ambient air and exhaled air within $V_{ds}$.

Once $\chi_{start\_of\_insp}$ is determined and/or estimated, estimation module 113 is configured to estimate the fraction of inhaled oxygen $FiO_2$ based on a comparison of an individual inhalation tidal volume $V_{ti}$ with a combination of the leaked inhalation volume $\int Q_{leak}$ during a particular individual inhalation and $V_{ds}$. Note that the particular individual inhalation may immediately follow the particular individual exhalation that was used to determine $\chi_{start\_of\_insp}$, as described previously. $FiO_2$ may be approximated using the following equation:

$$FiO2 = \frac{V_{ds} \cdot \chi_{start\_of\_insp} + \chi_{air} \int_{inspiration} Q_{leak}}{V_{ds} + \int_{inspiration} Q_{leak}} \quad \ldots \quad V_{ti} \leq \left(V_{ds} + \int_{inspiration} Q_{leak}\right)$$

$$FiO2 = \frac{V_{ds} \cdot \chi_{start\_of\_insp} + (V_{ti} - V_{ds}) \cdot \chi_{air}}{V_{ti}} \quad \ldots \quad V_{ti} > \left(V_{ds} + \int_{inspiration} Q_{leak}\right)$$

In some embodiments, information based on estimated fraction of inhaled oxygen $FiO_2$ may be displayed for presentation to subject 106 and/or user 108, e.g. through user interface 120. In some embodiments, $FiO_2$ may be compared to a predetermined minimum oxygen threshold, e.g. for individual inhalations. The predetermined minimum oxygen threshold may be about 19%, 19.5%, 20%, 20.1%, 20.2%, 20.3%, 20.4%, 20.5%, 20.6%, 20.7% and/or about another threshold of a mole fraction of oxygen, as may be suitable and/or appropriate for the operating conditions of system 10 and/or the condition of subject 106.

Estimation module 113 may be further configured to determine a fraction of inhaled carbon dioxide during individual inhalations, based on the estimated fraction of inhaled oxygen $FiO_2$, e.g. reciprocally. In other words, a decrease in the fraction of inhaled oxygen may correspond to an increase in the fraction of inhaled carbon dioxide.

Responsive to $FiO_2$ breaching the predetermined minimum oxygen threshold, system 10 and/or its constituent components may be configured to take one or more of the following actions: alarm and/or notify subject 106 and/or user 108, increase removal of carbon dioxide from system 10, reduce rebreathing, increase fall time, increase inhalation period, increase the positive end expiratory pressure level, and/or take other (corrective) actions and/or precautions. System 10 and/or its constituent components may be configured to take one or more of these actions in a predetermined order of escalation.

The positive end expiratory pressure may be set and/or raised to a predetermined PEEP level. Using a positive end expiratory pressure may reduce the probability of $FiO_2$ breaching the predetermined minimum oxygen threshold. An appropriate predetermined PEEP level may be based on various operating conditions of system 10, including the size of leak ports 183. The predetermined PEEP level may be about 2 $cmH_2O$, about 3 $cmH_2O$, about 3.5 $cmH_2O$, about 4 $cmH_2O$, about 4.5 $cmH_2O$, about 5 $cmH_2O$, and/or another pressure level. Monitoring $FiO_2$ as described herein may provide increased responsiveness to potential patient discomfort, e.g. when compared to traditional $SpO_2$ monitoring.

In a preferred embodiment, system 10 operates on a breath-by-breath basis. Note that this is not intended to be limiting. For example, in some embodiments, a fraction of inhaled oxygen may be estimated, determined, and/or aggregated over multiple inhalations and/or multiple exhalations.

Figure 2:
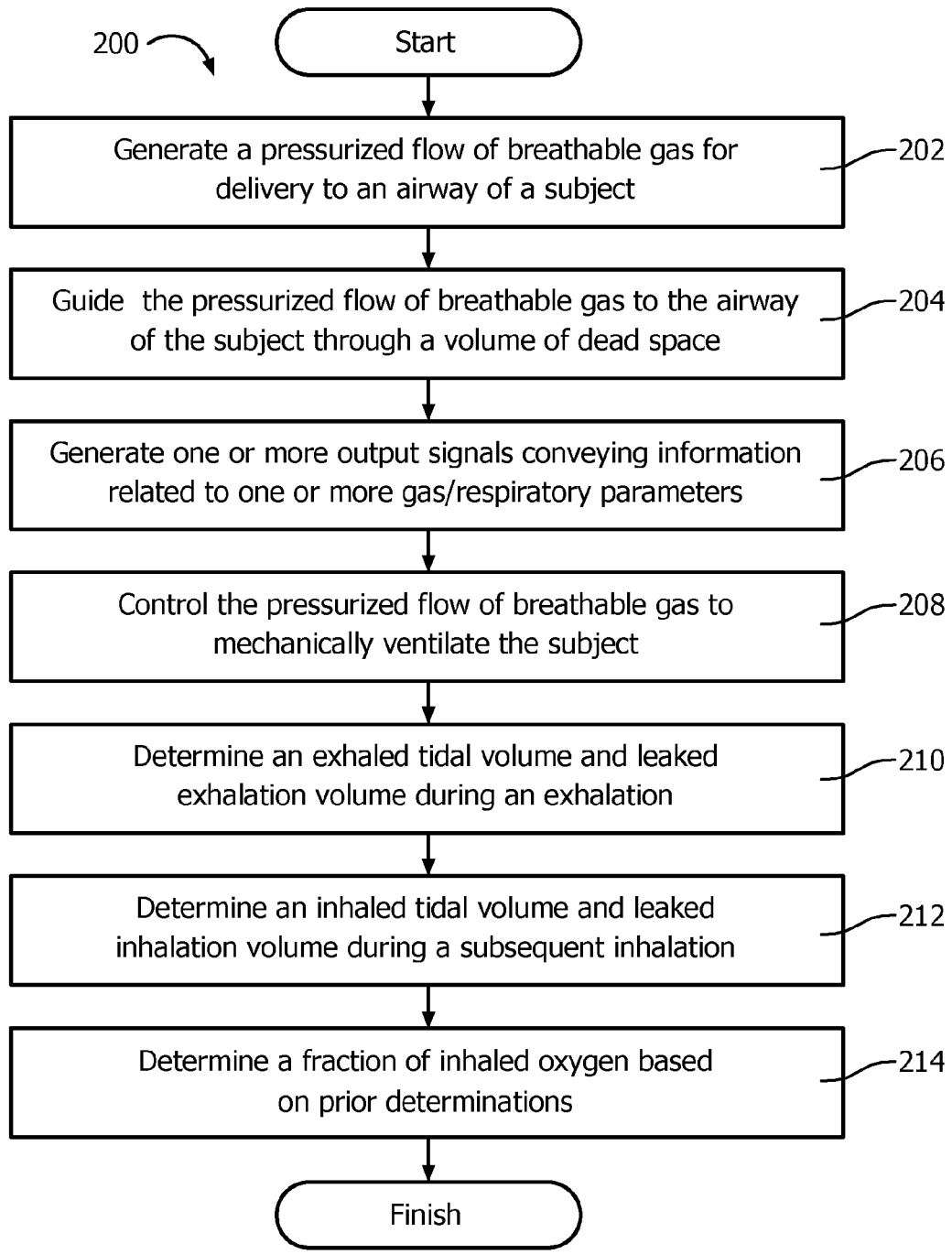
FIG. 2 illustrates a method of providing ventilation to a subject, according to one or more embodiments.

FIG. 2 illustrates a method 200 of ventilating a subject. The operations of method 200 presented below are intended to be illustrative. In some embodiments, method 200 may be accomplished with one or more additional operations not described, and/or without one or more of the operations discussed. Additionally, the order in which the operations of method 200 are illustrated in FIG. 2 and described below is not intended to be limiting.

In some embodiments, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

At an operation 202, a pressurized flow of breathable gas is generated for delivery to the airway of a subject. In some embodiments, operation 202 is performed by a pressure generator the same as or similar to pressure generator 140 (shown in FIG. 1 and described herein).

At an operation 204, the pressurized flow of breathable gas is guided to the airway of the subject through a volume of dead space. In some embodiments, operation 204 is performed by a delivery circuit the same as or similar to delivery circuit 180 (shown in FIG. 1 and described herein).

At an operation 206, one or more output signals are generated that convey information related to flow rate and/or pressure in the delivery circuit/subject interface. In some embodiments, operation 206 is performed by a sensor the same as or similar to sensor 142 (shown in FIG. 1 and described herein).

At an operation 208, the pressurized flow of breathable gas is controlled to at least partially mechanically ventilate the subject. In some embodiments, operation 208 is performed by a control module the same as or similar to control module 111 (shown in FIG. 1 and described herein).

At an operation 210, an exhaled tidal volume and leaked exhalation volume is determined during an exhalation. In some embodiments, operation 210 is performed by a parameter determination module the same as or similar to parameter determination module 112 (shown in FIG. 1 and described herein).

At an operation 212, an inhaled tidal volume and leaked inhalation volume is determined during a subsequent inhalation. In some embodiments, operation 212 is performed by a parameter determination module the same as or similar to parameter determination module 112 (shown in FIG. 1 and described herein).

At an operation 214, a fraction in inhaled oxygen is determined. The fraction of inhaled oxygen is based on a first comparison of the exhaled tidal volume with a combination of the volume of dead space and the leaked exhalation volume. The fraction of inhaled oxygen is further based on a second comparison of the inhaled tidal volume with a combination of the volume of the dead space and the leaked inhalation volume. In some embodiments, operation 214 is performed by an estimation module the same as or similar to estimation module 113 (shown in FIG. 1 and described herein).

It will be appreciated that the description of the operation of pressure generator 140 by the electronic processor 110 and/or its modules is not intended to be limiting. Other controllers for opening pressure generator 140 responsive to pressurization along delivery circuit 180 fall within the scope of this disclosure. Other mechanical controllers are also contemplated.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A ventilator comprising:
    a pressure generator configured to generate a pressurized flow of breathable gas for delivery to an airway of the subject;
    a subject interface configured to guide the pressurized flow of breathable gas to the airway of the subject, wherein the subject interface includes a volume of dead space;
    one or more sensors configured to generate output signals conveying information related to flow rate and/or pressure in the subject interface; and
    one or more processors configured to execute computer program modules, the computer program modules comprising:
        a control module configured to control the pressure generator to generate the pressurized flow of breathable gas to at least partially mechanically ventilate the subject;
        a parameter determination module configured to:
            determine, based on the output signals generated during an exhalation, an exhaled tidal volume and a leaked exhalation volume, and
            determine, based on the output signals generated during a subsequent inhalation, an inhaled tidal volume and a leaked inhalation volume; and
        an estimation module configured to estimate a fraction of inhaled oxygen during the subsequent inhalation based on a first comparison of the exhaled tidal volume with a combination of the volume of dead space and the leaked exhalation volume, and further based on a second comparison of the inhaled tidal volume with a combination of the volume of dead space and the leaked inhalation volume.

2. The ventilator of claim 1, wherein the control module is further configured to increase the positive end expiratory pressure level, responsive to the fraction of inhaled oxygen breaching a predetermined minimum oxygen threshold.

3. The ventilator of claim 1, further comprising one or more leak ports formed in the subject interface configured to provide fluid communication between an interior of the subject interface and ambient atmosphere to facilitate passive mechanical ventilation.

4. The ventilator of claim 1, wherein the estimation module is further configured to estimate a fraction of inhaled carbon dioxide during the subsequent inhalation based on the estimated fraction of inhaled oxygen.

5. The ventilator of claim 1, wherein the estimation module is further configured to estimate a mole fraction of oxygen in the volume of dead space based on the first comparison, wherein estimation of the fraction of inhaled oxygen is further based on the estimated mole fraction of oxygen in the volume of dead space.

6. A method of estimating a fraction of inhaled oxygen during provision of ventilation to a subject, the method comprising:
    generating a pressurized flow of breathable gas for delivery to an airway of the subject;
    guiding the pressurized flow of breathable gas to the airway of the subject through a volume of dead space;
    generating one or more output signals by one or more sensors conveying information related to flow rate and/or pressure of the pressurized flow of breathable gas;
    controlling the pressurized flow of breathable gas to at least partially mechanically ventilate the subject;
    determining, based on the output signals generated during an exhalation, an exhaled tidal volume and a leaked exhalation volume;
    determining, based on the output signals generated during a subsequent inhalation, an inhaled tidal volume and a leaked inhalation volume; and
    estimating a fraction of inhaled oxygen during the subsequent inhalation based on a first comparison of the exhaled tidal volume with a combination of the volume of dead space and the leaked exhalation volume, and further based on a second comparison of the inhaled tidal volume with a combination of the volume of dead space and the leaked inhalation volume.

7. The method of claim 6, further comprising increasing the positive end expiratory pressure level, responsive to the fraction of inhaled oxygen breaching a predetermined minimum oxygen threshold.

8. The method of claim 6, further comprising providing fluid communication between the volume of dead space and ambient atmosphere to facilitate passive mechanical ventilation.

9. The method of claim 6, further comprising estimating a fraction of inhaled carbon dioxide during the subsequent inhalation based on the estimated fraction of inhaled oxygen.

10. The method of claim 6, further comprising estimating a mole fraction of oxygen in the volume of dead space based on the first comparison, wherein estimating the fraction of inhaled oxygen during the subsequent inhalation is further based on the estimated mole fraction of oxygen in the volume of dead space.

11. A system configured for providing ventilation to a subject, the system comprising:
   pressure means for generating a pressurized flow of breathable gas for delivery to an airway of the subject;
   means for guiding the pressurized flow of breathable gas through a volume of dead space to the airway of the subject;
   sensor means for generating one or more output signals conveying information related to flow rate and/or pressure of the pressurized flow of breathable gas;
   control means for controlling the pressure means to at least partially mechanically ventilate the subject;
   means for determining, based on the output signals generated during an exhalation, an exhaled tidal volume and a leaked exhalation volume;
   means for determining, based on the output signals generated during a subsequent inhalation, an inhaled tidal volume and a leaked inhalation volume; and
   estimating means for estimating a fraction of inhaled oxygen during the subsequent inhalation based on a first comparison of the exhaled tidal volume with a combination of the volume of dead space and the leaked exhalation volume, and further based on a second comparison of the inhaled tidal volume with a combination of the volume of dead space and the leaked inhalation volume.

12. The system of claim 11, wherein the control means is further configured to increase the positive end expiratory pressure level, responsive to the fraction of inhaled oxygen breaching a predetermined minimum oxygen threshold.

13. The system of claim 11, further comprising means for providing fluid communication between the volume of dead space and ambient atmosphere to facilitate passive mechanical ventilation.

14. The system of claim 11, wherein the estimating means is further configured to estimate a fraction of inhaled carbon dioxide during the subsequent inhalation based on the estimated fraction of inhaled oxygen.

15. The system of claim 11, wherein the estimating means is further configured to estimate a mole fraction of oxygen in the volume of dead space based on the first comparison, and wherein operation of the estimating means to estimate the fraction of inhaled oxygen during the subsequent inhalation is further based on the estimated mole fraction of oxygen in the volume of dead space.

* * * * *